| United States Patent [19] | [11] Patent Number: 4,560,749 |
| Spry | [45] Date of Patent: Dec. 24, 1985 |

[54] CEPHEM-3-IMIDATES AND 3-AMIDINES

[75] Inventor: Douglas O. Spry, Mooresville, Ind.

[73] Assignee: Eli Lilly and Company, Indianapolis, Ind.

[21] Appl. No.: 552,960

[22] Filed: Nov. 18, 1983

[51] Int. Cl.$^4$ ............................................. C07D 501/18
[52] U.S. Cl. ........................................ 544/16; 544/19; 544/20; 544/22; 544/26
[58] Field of Search ..................... 544/16, 19, 20, 22, 544/26

[56] References Cited

U.S. PATENT DOCUMENTS 4,001,226  1/1977  Spry ................................. 424/246
4,101,658  7/1978  Yoshioka ........................... 424/246
4,307,233  12/1981  Farge ................................. 544/16

Primary Examiner—Donald G. Daus
Assistant Examiner—Robert Benson
Attorney, Agent, or Firm—William B. Scanlon; Arthur R. Whale

[57] ABSTRACT

3-Azido-3-cephem esters are reacted with electron rich olefins, e.g., enamines and cyclic enol ethers, to provide $C_3$ amidines and imidates having antibacterial activity in the free acid form. For example, 3-azido-3-cephem esters react with ethyl vinyl ether to provide 3-[1-(ethoxyethylidene)amino]-3-cephem esters. The latter are deesterified to provide the free acid antibacterials.

20 Claims, No Drawings

CEPHEM-3-IMIDATES AND 3-AMIDINES

BACKGROUND OF THE INVENTION

Cephalosporin semi-synthetic antibiotics substituted by an amino group in the 3-position of the 3-cephem ring system have been described by Spry, U.S. Pat. No. 4,001,226. Also described by Spry are 3-isocyanato, 3-azidocarbonyl, and 3-(substituted amino)carbonyl 3-cephem acids and esters.

In copending application Ser. No. 536,468 filed Sept. 28, 1983 (now U.S. Pat. No. 4521598), Spry and Spitzer describe 3-azido-3-cephem semi-synthetic antibiotics and the conversion thereof to 4,7-bicyclic diazabicyclononene antibiotic compounds. It has been found that the 3-azido-3-cephem compounds react with cyclic and acyclic vinyl ethers and with acyclic enamines to form, respectively, 3-cephem-3-imidates and 3-cephem-3-amidines wherein the nitrogen of the imidate and one nitrogen of the amidine group is bonded to the C3 carbon. Cyclic enol ethers and cyclic enamines react with the 3-cephem-3-azido compounds to provide bicyclic aziridines.

SUMMARY

Cephalosporin semi-synthetic antibiotics represented by the formula

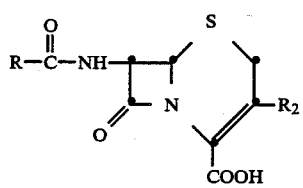

wherein $R_2$ is an imidate or amidine group

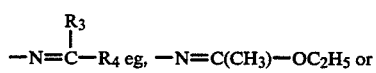

$-N=C-R_4$ eg, $-N=C(CH_3)-OC_2H_5$ or

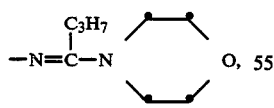

and R is the residue of a carboxylic acid, are prepared with 3-azido-cephalosporin esters ($R_2=N_3$) and acyclic vinyl ethers and enamines formed with aldehydes and cyclic secondary amines. Reaction of 3-azido-cephalosporins with cyclic enamines, for example the morpholine enamine of cyclohexanone and with cyclic enol ethers provide bicyclic aziridines where, in the above formula, $R_2$ is eg. a group represented by the formula

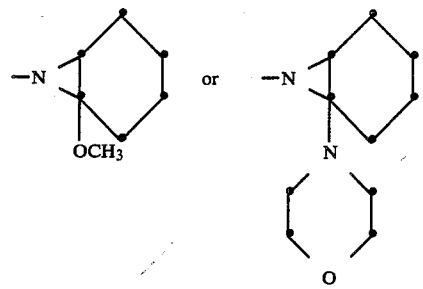

The compounds of the invention as the free acids or salts thereof inhibit the growth of micro-organisms pathogenic to man and animals and are useful for the control of such organisms.

DETAILED DESCRIPTION

The cephalosporin compounds provided by this invention are represented by the following structural formula 1

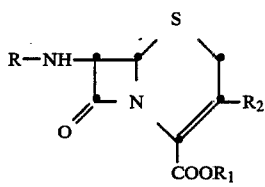

wherein R is hydrogen or an acyl group of the formula

wherein $R^1$ is hydrogen, $C_1$-$C_4$ alkyl, $C_1$-$C_4$ alkyl substituted by halogen or cyano;

or R is an aroyl or aralkanoyl group of the formula

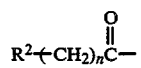

wherein $R^2$ is phenyl or a mono-substituted phenyl group of the formula

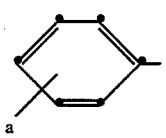

wherein a is halogen, amino, hydroxy, $C_1$-$C_4$ alkyl, $C_1$-$C_4$ alkoxy, cyano, hydroxymethyl, aminomethyl, carboxamido, carboxymethyl, or $C_1$-$C_4$ alkoxycarbonylmethyl;

or $R^2$ is a di- or tri-substituted phenyl group of the formula wherein a′, a″, and a‴ are independently hydrogen, halogen, hydroxy, $C_1$-$C_4$ alkyl, or $C_1$-$C_4$ alkoxy; and n is 0 or 1;

or R is a heteroarylalkanoyl group of the formula $$R^3-CH_2-\overset{O}{\underset{\|}{C}}-$$

wherein $R^3$ is wherein each b is amino, protected amino, $C_1$-$C_3$ alkyl or phenyl;

or R is an aryloxyacetyl or arylthioacetyl group of the formula $$R^2\!\!-\!\!(Z)\!\!-\!\!CH_2\!\!-\!\!\overset{O}{\underset{\|}{C}}-$$

wherein $R^2$ has the same meanings as defined above and Z is O or S;

or R is an α-substituted aralkanoyl or heteroarylalkanoyl substituted group of the formula $$R^4-\underset{\underset{Q}{|}}{CH}-\overset{O}{\underset{\|}{C}}-$$

wherein $R^4$ is $R^2$, as defined above, and in addition is thienyl, furyl, or 1,4-cyclohexadienyl; Q is hydroxy, formyloxy, carboxy, the sulfo group —$SO_3H$, or amino;

or R is an oximino-substituted aralkanoyl or heteroarylalkanoyl group of the formula $$R^5-\underset{\underset{N}{\|}}{C}-\overset{O}{\underset{\|}{C}}-$$

$$OR^6$$

wherein $R^5$ is $R^2$ and $R^3$ as each is defined above, and $R^6$ is hydrogen or $C_1$-$C_3$ alkyl;

$R_1$ is hydrogen or a carboxy-protecting group;

$R_2$ is a group represented by the formula 1A $$-N=\underset{\underset{R_3}{|}}{C}-R_4 \quad\quad 1A$$

wherein $R_3$ when taken separately is $C_1$-$C_4$ alkyl or $C_1$-$C_4$ alkyl substituted phenyl or substituted phenyl;

$R_4$ when taken separately is $C_1$-$C_4$ alkoxy, $C_1$-$C_4$ alkylthio; phenoxy, substituted phenoxy, phenylthio, and substituted phenylthio; or $R_4$ is an amino group represented by the formula $$-N\!\!\diagdown\!\!\overset{R_4'}{\underset{R_4''}{}}$$

wherein $R_4'$ and $R_4''$ are independently $C_1$-$C_4$ alkyl, phenyl or substituted phenyl, and $R_4'$ and $R_4''$ when taken together with the nitrogen atom to which they are attached form a 5–7 membered heterocyclic ring represented by the formula wherein Y is (—$CH_2$—)$_{n'}$, or —$CH_2$—Y′—$CH_2$— wherein n′ is 2 or 3 and Y′ is O, S, or $$-\underset{|}{N}-Y'';$$

wherein Y″ is hydrogen, $C_1$-$C_4$ alkyl, or benzyl.

$R_3$ and $R_4$ when taken together with the carbon atom to which they are attached form a 5–7 membered ring represented by the formula wherein Z′ is O or S and m is 2 to 4; or $R_2$ is a group represented by the formula 1B

1B wherein m and Z' have the same meanings as defined above; or R₂ is a bicyclic aziridino group represented by the formula 1C

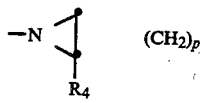

wherein p is 3–5, and R₄ has the same meanings as defined above; and when R₁ is hydrogen, the pharmaceutically acceptable non-toxic salts thereof.

In the above formula the term, $C_1$–$C_4$ alkyl refers to the straight chain and branched chain lower alkyl radicals such as methyl, ethyl, n-propyl, isopropyl, n-butyl, and t-butyl; halogen refers to fluoro, chloro, bromo, and iodo; and $C_1$–$C_4$ alkoxy refers to methoxy, ethoxy, n-propoxy, isopropoxy, n-butoxy, and t-butoxy; substituted phenyl refers to a phenyl group substituted by one or two of halogen, $C_1$–$C_4$ alkyl, hydroxy, $C_1$–$C_4$ alkoxy, carboxy, carboxamido, or cyano, for example, 4-chlorophenyl, 3-bromophenyl, 3-chloro-4-hydroxyphenyl, 2,4-dimethylphenyl, 4-t-butylphenyl, 3,4-dimethoxyphenyl, 2-fluorophenyl, 4-ethoxyphenyl, 3-cyanophenyl, 4-carboxyphenyl, 2-carboxyphenyl, 4-carbamoylphenyl, and the like. The term $C_1$–$C_4$ alkyl substituted by phenyl or substituted phenyl, R₃, refers to groups such as benzyl, 1-phenylethyl, 2-phenylethyl, 3-phenylpropyl, 4-phenylbutyl, 3-phenylbutyl, 2-(4-methylphenyl)ethyl, 4-ethylbenzyl, 3,4-dichlorobenzyl, 4-methoxybenzyl, 3-(3-carboxyphenyl)propyl, 2-cyanobenzyl, 4-(3-chloro-4-hydroxyphenyl)butyl, and like groups. The term $C_1$–$C_4$ alkylthio (R₄) refers to methylthio, ethylthio; n-propylthio; n-butylthio; and the like. Substituted phenoxy and substituted phenylthio refer to phenoxy and phenylthio groups wherein the phenyl ring is mono or disubstituted as defined hereinabove, eg., 4-chlorophenoxy, 4-chlorophenylthio, 3-bromophenoxy, 4-fluorophenylthio, 3,4-dimethylphenylthio, 3,4-dichlorophenoxy, 4-ethylphenoxy, 3-carboxyphenoxy, 4-cyanophenoxy, 2-fluorophenoxy, 3,4-dimethoxyphenoxy, 2-ethoxyphenoxy, 4-t-butoxyphenylthio; 4-methoxyphenylthio, 3-hydroxyphenoxy, 4-hydroxyphenoxy, 4-hydroxyphenylthio and like groups.

Examples of acyl group represented by R in the formula 1 when R is R'—C(O)— are formyl, acetyl, propionyl, butryl, chloroacetyl, and cyanoacetyl; when R is an aroyl or aralkanoyl group, examples include benzoyl, 4-chlorobenzoyl, 2,6-dimethoxybenzoyl, 4-hydroxybenzoyl, 4-methylbenzoyl, 4-methoxybenzoyl, 3,4-dichlorobenzoyl, 3-cyanobenzoyl, 4-methoxycarbonylmethylbenzoyl, 4-ethylbenzoyl, 4-bromo-3-methylbenzoyl, 4-t-butylbenzoyl, 2-fluorobenzoyl, 3-hydroxybenzoyl, 4-carbamoylbenzoyl, 2-aminomethylbenzoyl, 3-ethoxybenzoyl, phenylacetyl, 4-chlorophenylacetyl, 4-methylphenylacetyl, 4-hydroxyphenylacetyl, 3,4-dimethylphenylacetyl, 2-aminomethylphenylacetyl, 4-methoxyphenylacetyl, 2,6-dimethoxyphenylacetyl, 4-ethoxyphenylacetyl, 3-bromophenylacetyl, 3,4-dihydroxyphenylacetyl, 3,5-dichloro-4-hydroxyphenylacetyl, 3-chloro-4-hydroxyphenylacetyl, 3-ethoxy-4-hydroxyphenylacetyl, 4-cyanophenylacetyl, 4-carboxyphenylacetyl, 4-carboxymethylphenylacetyl, 4-t-butylphenylacetyl, 3,4,5-trihydroxyphenylacetyl, and 3-bromo-4-ethoxyphenylacetyl; and when R is a heteroarylalkanoyl group, examples of R include 2-thienylacetyl, 3-thienylacetyl, 2-furylacetyl, 1H-tetrazol-1-ylacetyl, 2H-tetrazol-5-ylacetyl, thiazol-4-ylacetyl, oxazol-4-ylacetyl, 2-methylthiazol-4-ylacetyl, 2-aminothiazol-4-ylacetyl, and 2-phenyloxazol-4-ylacetyl; and when R is an aryloxyacetyl or arylthioacetyl group, examples include phenoxyacetyl, 4-chlorophenoxyacetyl, 3,4-dichlorophenoxyacetyl, 4-methylphenylacetyl, 4-fluorophenoxyacetyl, 4-hydroxyphenoxyacetyl, 3-chloro-4-methoxyphenoxyacetyl, 4-ethoxyphenoxyacetyl, phenylthioacetyl, 4-chlorophenylthioacetyl, 3,5-dichlorophenylthioacetyl, 4-fluorophenylthioacetyl, 3,4-dichlorophenylthioacetyl, 4-bromophenylthioacetyl, and 4-chloro-3-methylphenylthioacetyl; and when R is an α-substituted aralkanoyl or heteroarylalkanoyl group, examples include phenylglycycl, 4-hydroxyphenylglycyl, 4-ethoxyphenylglycyl, 4-chlorophenylglycyl, 3-chloro-4-hydroxyphenylglycyl, 2-thienylglycyl, mandeloyl, malonyl, α-sulfophenylacetyl, and α-amino-1,4-cyclohexadien-1-ylacetyl; and when R is an oximino-substituted acyl group, examples of such groups are α-hydroxyiminophenylacetyl, α-methoximinophenylacetyl, α-methoximino-2-furylacetyl, α-methoximino-2-thienylacetyl, α-hydroxyimino-(2-aminothiazol-4-yl)acetyl, and α-methoximino-(2-aminothiazol-4-yl)acetyl.

The term "protected amino" as used herein refers to the amino group substituted by a conventional amino protecting group commonly used in the cephalosporin and peptide arts. Examples of such groups are the alkyloxycarbonyl and aralkyloxycarbonyl groups such as methoxycarbonyl, ethoxycarbonyl, t-butoxycarbonyl BOC, trichloroethoxycarbonyl, benzyloxycarbonyl, p-nitrobenzyloxycarbonyl, and diphenylmethoxycarbonyl; the alkenyloxycarbonyl and alkinyloxycarbonyl groups, eg., allyloxycarbonyl and the dialkylethinylcarbinyloxycarbonyl groups, such as dimethylethinylcarbinyloxycarbonyl; the cycloalkoxycarbonyl groups, eg., cyclopentyloxycarbonyl and cyclohexyloxycarbonyl; the β-ketoesters which form enamines with the amino group, eg., ethyl acetoacetate and methyl acetoacetate; the aryl-protecting groups such as trityl; the silyl-protecting groups, eg., trialkylsilyl such as trimethylsilyl and dimethylbutylsilyl; acyl and diacyl groups such as acetyl, chloroacetyl, and phthaloyl; and other commonly used amino-protecting groups.

The term "carboxy-protecting group" refers herein to the ester-forming groups which are readily removable under mild hydrolysis or hydrogenolysis conditions, and which are commonly employed in the β-lactam and polypeptide arts for the temporary protection of the carboxy group. Examples of such groups are the alkyl and substituted-alkyl group, eg., t-butyl, 2,2,2-trichloroethyl, 2,2,2-tribromoethyl, and 2-iodoethyl; the aralkyl groups such as benzyl, 4-nitrobenzyl, 4-methoxybenzyl, and diphenylmethyl; the trialkylsilyl groups such as trimethylsilyl, triethylsilyl, and dimethyl-t-butylsilyl; phenacyl and substituted-phenacyl groups; the N-oxysuccinimido and N-oxyphthalimido groups; and like ester-forming groups.

The compounds of the invention in the free acid form (R₁=H) form salts with suitable bases. For example, salts can be formed with the alkali metal and alkaline earth metal hydroxides, carbonates and bicarbonates such as sodium hydroxide, potassium hydroxide, calcium hydroxide, sodium carbonate, sodium bicarbonate, potassium carbonate and potassium bicarbonate. Such sodium, potassium, calcium, and like salts are pharmaceutically acceptable salts which possess the anti-bacterial activity of the free acid form. Salts may also be formed with pharmaceutically acceptable amines and ammonia. Suitable amines include benzylamine, dibenzylamine, cyclohexylamine, dicyclohexylamine, hydroxyalkylamines such as 2-hydroxyethylamine, 3-hydroxypropylamine, and di(2-hydroxyethyl)amine, ethylamine, diethylamine, n-butylamine, di(n-butyl)amine, and like salts. Such salts can be used in formulating the compounds of the invention or they also may be useful in isolating and purifying the compounds of the invention. The salts can be prepared by known procedures for preparing salts of carboxylic acids.

The compounds of the invention are prepared by reacting a 3-azido-3-cephem ester represented by the formula 2

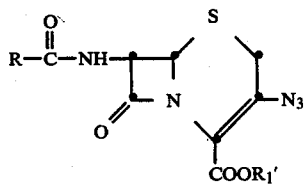

wherein R has the same meanings as defined hereinabove and $R_1'$ is a carboxy-protecting group; with an electron-rich olefin selected from an acyclic or cyclic vinyl ether, a cyclic enol ether, and an acylic or cyclic enamine. The compounds wherein $R_2$ (formula 1) is the group 1A and $R_3$ and $R_4$ are each taken separately are obtained by reacting the azido cephem (2) with an acyclic vinyl ether wherein $R_4$ is $C_1-C_4$ alkoxy, $C_1-C_4$ alkylthio, phenoxy, substituted phenoxy, phenylthio or substituted phenylthio. The vinyl ether may be represented by the formula $R_3'$—CH=CH—$R_4$ wherein $R_3'$ is hydrogen, $C_1-C_3$ alkyl or $C_1-C_3$ alkyl substituted by phenyl or substituted phenyl, and $R_4$ is as defined above for formula 1. When in the formula 1 $R_4$ is a substituted amino group —N($R_4'$)($R_4''$) and $R_4'$ and $R_4''$ are taken separately the compounds of the invention are prepared with an enamine of an acyclic secondary amine and an aldehyde represented by the formula

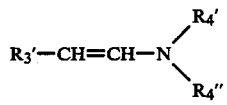

wherein $R_3'$, $R_4'$ and $R_4''$ are as defined above. When $R_4'$ and $R_4''$ are taken together the 3-azido cephem (2) is reacted with an enamine formed with an aldehyde and a cyclic N-heterocyclic represented by the formula

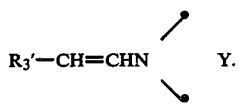

Examples of vinyl ethers which can be used are methylvinyl ether, ethylvinyl ether, n-propylvinyl ether, 1-methoxybutene, 1-ethoxybutene, 1-t-butoxypropene, methylvinyl thioether (CH$_3$S—CH=CH$_2$), ethylvinyl thio ether, phenylvinylether, 4-methylphenylvinyl ether, 4-methoxyphenylvinyl ether, 1-phenoxypropene, 1-phenoxybutene, phenylvinyl thioether, 1-phenylpropene thioether, 3,4-dimethoxyphenyl vinyl thioether and like ethers. Examples of the enamines which can be used are those formed with the nitrogen heterocyclics morpholine, thiomorpholine, pyrrolidine, piperidine, hexamethyleneimine and N-methylpiperazine, and a $C_2-C_5$ alkyl aldehyde or a phenyl or substituted phenyl $C_2-C_5$ aldehyde. Examples of such enamines include those formed with, acetaldehyde and morpholine, piperidine, thiomorpholine and pyrrolidine; propionaldehyde and morpholine, thiomorpholine, hexamethyleneimine, piperidine, N-methylpiperazine, n-butyraldehyde and pyrrolidine, piperidine, morpholine, hexamethyleneimine; n-valeraldehyde and piperidine, morpholine, N-methylpiperazine; and isovaleraldehyde with morpholine, piperidine and thiomorpholine; phenylacetaldehyde and thiomorpholine, 4-methoxyphenylacetaldehyde and N-ethylpiperazine, 3,4-dichlorophenylacetaldehyde and piperidine, and 3-(3-hydroxyphenyl)propionaldehyde and morpholine. Examples of enamines used in the preparation of formula 1 compounds wherein $R_4'$ and $R_4''$ are taken separately include the enamine formed with acetaldehyde and diethylamine, acetaldehyde and N-methylaniline, 2-phenylpropionaldehyde and di-n-butylamine, propionaldehyde and methylethylamine, n-butyraldehyde and diphenylamine, and the like.

The electron-rich olefin may be a cyclic olefin for example, the compounds of the formula 1 wherein $R_2$ is a group of the formula —N=C—($R_3$)($R_4$) and $R_3$ and $R_4$ are taken together to form a cyclic group

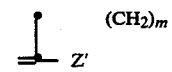

are prepared with the 3-azido-3-cephem and cyclic vinyl ethers. Examples of such cyclic ethers are dihydrofuran, dihydropyran, dihydrothiopyran, oxacyclohep-2-ene (2-oxepene), and the like.

The 3-bicyclic aziridino-substituted compounds represented by the formula 1 wherein $R_2$ is a group of the formula 1C

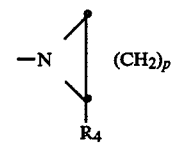

and $R_4$ is $C_1-C_4$ alkoxy, $C_1-C_4$ alkylthio, phenoxy, substituted phenoxy, phenylthio or substituted phenylthio, are prepared with the 3-azido-3-cephem (2) and a cyclic enol ether represented by the formula

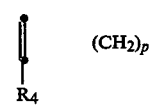

wherein $R_4$ is the above named alkyl and phenyl ether and thioether groups. The cyclic enol ether may be, for example, 1-methoxycyclopentene, 1-ethoxycyclohexene, 1-isopropoxycyclohexene, 1-methoxycycloheptene, 1-phenoxycyclopentene, 1-phenylthiocyclohexene, 1-methylthiocyclohexene, 1-n-butoxycyclopentene, and like enol ethers.

The 3-aziridino-substituted compounds wherein $R_4$ is a heterocyclic ring

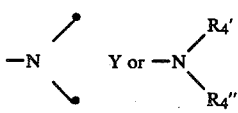

as defined hereinabove are prepared with the 3-azido-3-cephem ester and an enamine of a cyclic ketone. Examples of such enamines are those formed with cyclopentanone, cyclohexanone, and cycloheptanone and the heterocyclics pyrrolidine, piperidine, hexamethyleneimine, morpholine, thiomorpholine, and N-methylpiperazine or an acyclic amine such as diethylamine or dibutylamine. The aziridino group 1C is exemplified by that formed with the morpholine enamine of cyclohexanone as follows.

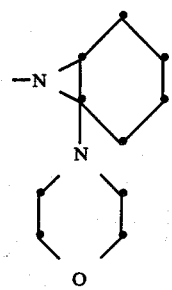

The compounds represented by the formula 1 wherein $R_2$ is represented by the formula 1B

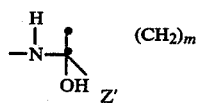

are prepared with the compounds wherein $R_2$ is the group

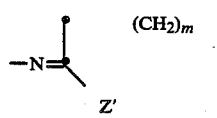

The latter compound undergoes hydration over silica gel to provide the hydroxylated compound wherein $R_2$ is 1B. The hydration can occur during the chromatographic purification of the compound

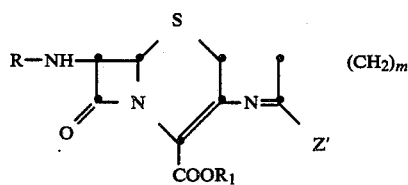

Alternatively, the hydroxylation of the cyclic 1A of the above general formula may be carried out indirectly. The compound is first methoxylated by heating the compound with methyl alcohol at the reflux temperature. The alcohol adds across the imine double bond. Chromatography over silica gel of the methyl alcohol adduct provides the hydroxyl derivative wherein $R_2$ is the group 1B.

The preparation of the compounds of the invention is carried out in an inert solvent with an ester of a 3-azido-3-cephem (2) wherein $R_1'$ is a carboxy-protecting group, and the reactant acyclic or cyclic enamine, the acyclic or cyclic vinyl ether, or the cyclic enol ether. In general, the reaction is carried out at a temperature between about 20° C. and about 75° C. The reaction of the 3-azido cephalosporin with an acyclic or cyclic vinyl ether is preferably carried out at a temperature of about 50° C. to about 60° C. while the enamines react at or about room temperature.

Solvents used in the reaction are common organic solvents which are unreactive towards both the azido group and the reactant ethers and enamines. Solvents such as the halogenated hydrocarbons eg. chloroform, methylene chloride, and di and trichloroethanes may be used. When the vinyl ethers and enol ethers are the desired reactants, ketones, esters and ethers may be used. For example, acetone, methylisobutyl ketone, methylethyl ketone, ethyl acetate, tetrahydrofuran, dioxane, and like solvents can be used. Likewise, such unreactive solvents can also be used when an enamine is the electron rich olefin reactant. Low boiling solvents are preferred since they are easy to remove from the reaction mixture after the reaction is completed.

The compound of the invention is recovered from the reaction mixture and the product(s) purified by column chromatography, preferably over silica gel. In general, the reaction mixture is evaporated to dryness and the reaction product mixture chromatographed over silica gel. Preferably, the gradient elution technique is used by employing a toluene-ethyl acetate gradient of increasing polarity.

The product of the reaction is an ester represented by the formula 1 wherein $R_1$ is a carboxy-protecting group. The product is deesterified by known methods to obtain the product in its active free acid form (formula 1, $R_1$=H or a salt thereof). The deesterification of the carboxy-protecting group can be carried out by chemical means such as acidic hydrolysis, chemical reduction, catalytic hydrogenolysis, or enzymatically. Carboxy-protecting groups such as the diphenylmethyl and p-methoxybenzyl group can be removed by treatment of the ester with trifluoroacetic acid in the presence of anisole. The 2,2,2-trichloroethyl group and the p-nitrobenzyl group can be removed by reduction with zinc and formic acid. The allyl ester can be removed with the reagent $Pd(P\phi_3)_4$ prepared with palladium diacetate and triphenylphosphine and tri-n-butyltin hydride, details of which are provided hereinafter in the Examples. The lower alkyl esters ($R_1$) although not normally recognized as readily removable carboxy-protecting ester groups, can be removed enzymatically to provide the free carboxylic acid. Chicken liver esterase is a suitable enzyme. The esterase is prepared by grinding up whole chicken livers in pH 7 phosphate buffer, eg., in a blender, and centrifuging the blend to separate particulate matter from the enzyme-containing liquid. The crude preparation need not be further purified for use. The ester of the formula 1 is then incubated with the crude esterase preparation maintained at about pH 7 and at about 35° C. to about 40° C. The free acid form of the compound can be recovered from the deesterification mixture by extraction with an aqueous solution of an alkali metal hydroxide, carbonate, or bicarbonate.

The compounds of the invention in free acid form inhibit the growth of various gram-positive and gram-negative bacteria. Table 1 below shows the activity of two compounds of the invention where in formula 1 R is 2-thienylacetyl.

TABLE I

| | In Vitro Antibacterial Activity Disc-Plate Method | | | |
|---|---|---|---|---|
| | Test Compound[1] Zone of Inhibition, Size (mm diam) | | | |
| | A | | B | |
| | (concentration mg/ml) | | | |
| Test Organism | 4 | 1 | 5 | 0.8 |
| Staphylococcus aureus | 43 | 39 | 39 | 36 |
| Bacillus subtilis[2] | 43 | 37 | 42 | 33 |
| Bacillus subtilis | 30 | 26 | 29 | 25 |
| Bacillus stearothyermophilus | 25 | 19 | 24 | 24 |
| Micrococcus luteus | 34 | 30 | 35 | 31 |
| Mycobacterium smegmatis | 37 | 32 | — | — |
| Saccharomyces partorianus | — | — | t[3] | |
| Candida albicans | — | — | t | |
| Trichophyton mentagrophytes | — | — | t | |
| Proteus vulgaris | 14 | 2 | 16 | t |
| Escherichia coli[2] | 18 | 10 | 20 | 10 |
| Escherichia coli | 15 | t[3] | 40 | 30 |

[1]A is 7β-(2-thienylacetylamino)-3-[1-4-morpholinyl)-butylideneamino]-3-cephem-4-carboxylic acid
B is 7β-(2-thienylacetylamino)-3-[1-(ethoxyethylidene)-amino]-3-cephem-4-carboxylic acid
[2]Microorganism grown on minimal medium
[3]t = trace zone of inhibition.
A dash indicates not tested and a blank indicates no observed zone of inhibition.

The antibacterial compounds of the invention can be used to prepare antiseptic solutions for topical application. Such solutions may contain a compound of the formula 1 (wherein R is an acyl group and $R_1$ is hydrogen or a salt thereof) at a concentration of from about 1% to about 20%. The compound or a pharmaceutically-acceptable non-toxic salt thereof may be formulated with a pharmaceutically-acceptable diluent such as water, isopropanol, ethanol, or mixtures thereof and also may contain solubilizing agents, stabilizers, coloring agents, and like excipients. The solution may be used to prevent or control skin infections by treating cuts, abrasions, burns, and contusions.

The compounds of the invention where in formula 1 R is hydrogen are obtained with a 7-amino-3-azido-3-cephem ester by following the reaction procedures and conditions described hereinabove for the preparation of formula 1 compounds wherein R is an acyl group. The 7-amino-3-substituted compounds of the invention are useful as intermediates for the formula 1 compounds wherein R is an acyl group. The 7-amino compound can be acylated with an active derivative of the carboxylic acid forming the desired acylamino group. The acylation is carried out by following well known procedures for coupling a carboxylic acid with an amine to form an amide. The general procedures employed for the acylation of 7ACA and 7ADCA can be used. "Active derivatives" of the carboxylic acid include for example, acid halides, acid azides, anhydrides, and active esters such as those formed with the acid and methyl chloroformate and isobutyl chloroformate. The acid and 7-amino compound may be coupled in the presence of a dehydrating agent such as a carbodiimide, eg., dicyclohexylcarbodiimide.

The 7-amino nucleus compounds (formula 1 $R_1=H$) can be obtained in the form of a salt formed with a hydrohalide acid such as hydrochloric acid and hydrobromic acid, or with sulfuric acid or phosphoric acid. Salts may also be formed with sulfonic acids such as with an alkylsulfonic acid, eg., methanesulfonic acid, n-butanesulfonic acid, or an arylsulfonic acid, eg., benzenesulfonic acid, toluenesulfonic acid, or naphthalenesulfonic acid.

A preferred group of compounds of this invention are represented by the formula 1 wherein $R_2$ is a group of the formula

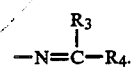

A further preferred group is represented when $R_4$ is $C_1$-$C_4$ alkoxy or a 5 to 7-membered heterocyclic ring as defined for $R_4$. Another preferred group $R_2$ is represented by the formula

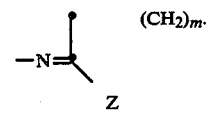

The following Examples are provided to further illustrate the invention as described herein.

Preparation of 3-azido-3-cephem esters

Preparation 1

Allyl 7β-(2-thienylacetamido)-3-azido-3-cephem-4-carboxylate

To a solution of 0.409 g. of allyl 7β-(2-thienylacetaimdo)-3-chloro-3-cephem-4-carboxylate in 20 ml. of dimethylformamide cooled to about 5° C. in an ice bath were added 0.073 g. (1.1 eq.) of sodium azide. The reaction mixture was stirred in the cold for 1.5 hr. and then was transferred to a separatory funnel with cold ethyl acetate. The mixture was washed five times with water, once with brine, dried over sodium sulfate and evaporated to dryness in vacuo at 30° C. There were obtained 0.389 g. (94%) of the 3-azido compound.

IR (chloroform): 2100 and 1780 cm$^{-1}$

NMR (T-60, CDCl$_3$): δ3.58 (s, 2H, C$_2$-H), 3.83 (s, 2H, side chain CH$_2$), 4.72 (m, 2H, allyl CH$_2$), 4.93 (d J=4 Hz, 1H, C$_6$-H), 5.2–5.6 (m, 3H, allyl), 5.75 (d, d J=4, 8 Hz, 1H, C$_7$-H), and 7.50 (d, 1H, NH).

Preparation 2 p-Nitrobenzyl 7β-(2-thienylacetamido)-3-azido-3-cephem-4-carboxylate

To a solution of 0.554 g. of p-nitrobenzyl 7β-(2-thienylacetamido)-3-methylsulfonyloxy-3-cephem-4-carboxylate in 10 ml. of DMF was added one molar equivalent (0.065 g.) of sodium azide and the mixture stirred at room temperature for 30 minutes. The mixture was transferred to a separatory funnel with ethyl acetate and the solution was washed three times with water, once with brine, dried over sodium sulfate and evaporated to dryness. The product, 0.523 g. obtained as a yellow froth, showed a single spot on silica gel thin layer chromatography using 1:1, ethyl acetate:toluene for development and iodine for visualization.

Preparation 3

Methyl 7β-(2-thienylacetamido)-3-azido-3-cephem-4-carboxylate

A twenty-gram mixture of methyl 7β-(2-thienylacetamido)-3-chloro-3-cephem-4-carboxylate and the corresponding 2-cephem isomer was dissolved in 100 ml. of DMF, the solution cooled to about 5° C. in an ice bath, and 1.1, eg., (3.84 g.) of sodium azide were added. The reaction mixture was stirred at 5° C. for 30 minutes and for one hour without cooling. The reaction mixture was transferred to a separatory funnel with ethyl acetate and washed five times with water, once with brine, dried and evaporated to dryness to yield 19.5 g. of crude product as a brown solid.

IR (CHCl$_3$): 2100 cm$^{-1}$ (azide), 1770 cm$^{-1}$ (β-lactam carbonyl).

U.V. $\lambda_{max}$ 296 nm $\epsilon$=8,000 (ethanol).

NMR (T60, CDCl$_3$): δ 3.57 (br. s, 2H, C$_2$-H), 3.87 (s, 2H, side chain methylene), 4.97 (d, J=4 Hz, 1H, C$_6$-H), 5.70 (d, d J=4, 8 Hz, 1H, C$_7$-H).

Preparation 4

Diphenylmethyl 7β-phenoxyacetamido-3-azido-3-cephem-4-carboxylate

To a solution of 1.728 g. of diphenylmethyl 7β-phenoxyacetamido-3-chloro-3-cephem-4-carboxylate in 25 ml. of DMF were added 1.05, eg., (0.220 g.) of sodium azide and the mixture was stirred at room temperature for one hour. The reaction mixture was transferred to a separatory funnel with ethyl acetate and washed three times with water, once with brine, dried, and evaporated to dryness. The crude product was purified by chromatography over 15 g. of silica gel using 500 ml. of toluene vs. 500 l. of 1:1 ethylacetate:toluene for elution. Multiple fractions were collected with fractions 24 to 31 being combined. The pooled fractions were evaporated to dryness to yield 0.795 g. of product as a yellow froth.

IR (CHCl$_3$) 2105 cm$^{-1}$, 1785 cm$^{-1}$.

NMR (CDCl$_3$): δ 2.80, 3.27 (ABq J=16 Hz, 2H, C$_2$-H), 4.57 (s, 2H, side chain CH$_2$), 4.92 (d, J=4 Hz, 1H, C$_6$-H), 5.60 (d, d J=4, 8 Hz, 1H, C$_7$-H.

Preparation 5

2,2,2-Trichloroethyl 7β-(2-thienylacetamido)-3-azido-3-cephem-4-carboxylate

To a solution of 2.926 g. of 2,2,2-trichloroethyl 7β-(2-thienylacetamido)-3-chloro-3-cephem-4-carboxylate in 17 ml. of DMF was cooled to 5° C. in an ice bath and 0.427 g. of sodium azide were added. The reaction mixture was stirred in an ice bath for 2 hours and was then transferred to a separatory funnel with ethyl acetate. The mixture was washed with water and brine, dried and evaporated to dryness. There were obtained 2.54 g. of the crude 3-azido product.

IR (CHCl$_3$) 2110, 1788 cm$^{-1}$

UV $\lambda_{max}$ 300 nm $\epsilon$=3,800 (ethanol).

NMR (T-60, CDCl$_3$): δ 3.58 (s, 2H, C$_2$-H), 3.85 (s, 2H, side chain CH$_2$), 4.75, 4.98 (ABq J=11 Hz, 2H, ester), 5.00 (d, J=4 Hz, 1H, C$_6$-H), 5.73 (d, d J=4, 8 Hz, 1H, C$_7$-H).

Preparation 6

Methyl 7β-acetamido-3-azido-3-cephem-4-carboxylate

A solution of 0.784 g. of methyl 7β-acetamido-3-chloro-3-cephem-4-carboxylate in 40 ml. of DMF was cooled to 5° C. in an ice bath and 0.193 g. of sodium azide were added. The reaction mixture was stirred in the cold for 45 minutes and then transferred to a separatory funnel with ethyl acetate. The mixture was washed with cold water, with brine, and was dried and evaporated to dryness. There were obtained 0.581 g. of the 3-azido ester product as a yellow solid.

EXAMPLE 1

7β-(2-Thienylacetylamino)-3-[1-(ethoxyethylidene)amino]-3-cephem-4-carboxylic acid To a solution of allyl 0.719 g. of 7β-(2-thienylacetylamino)-3-azido-3-cephem-4-carboxylate in 25 ml. of acetone were added 25 ml. of ethyl vinyl ether (large excess) and the solution was heated at the reflux temperature for 60 minutes. The reaction mixture was evaporated to dryness and the residue chromatographed on silica gel using 400 ml. of toluene vs. 400 ml of ethyl acetate. Multiple fractions were collected and fractions containing only the product (via tlc) were pooled and evaporated to yield 0.06 g. of allyl 7β-(2-thienylacetylamino)-3-[1-(ethoxyethylidene)amino]-3-cephem-4-carboxylate.

Mass Spectra (field desorption) 449.

IR (CHCl$_3$) 1775 cm$^{-1}$ (β-lactam carbonyl).

UV (C$_2$H$_5$OH): $\lambda_{max}$ 232 nm ($\epsilon$=12,700); $\lambda_{max}$ 290 nm ($\epsilon$=6,500).

NMR (T-60, CDCl$_3$): δ 1.27 (t, 3H, O—CH$_2$CH$_3$), 1.90 (s, 3H, N=C—CH$_3$), 3.27 (s, 2H, C$_2$H), 3.83 (s, 2H, —CH$_2$-thienyl), 4.00, 4.22 (AB J=6 Hz, 2H, CH$_2$—CH$_3$), 4.67 (m, 2H, —O—CH$_2$CH=CH$_2$), 5.00 (d, J=4 Hz, 1H, C$_6$H), 5.2-5.4 (m, 3H, ally vinyl H), 5.57 (d, d J=4.8 Hz, 1H, C$_7$H).

The allyl ester product was deesterified to the free acid as follows. To a solution of 1.6 mg. palladium diacetate in 1 ml. of acetone was added 0.125 equivalents of triphenylphosphine and the solution was stirred at room temperature for 5 minutes to form Pd(Pϕ$_3$)$_4$. To the solution was added a solution of 60 mg. of the allyl ester product in about 2 ml. of acetone and the mixture was stirred for 10 minutes at 5° C. Trin-butyltin hydride (0.043 ml.) was added and the reaction mixture was stirred at 5° C. for 30 minutes. The mixture was evaporated to dryness at 40° C., the residue dissolved in cold acetonitrile, and the solution washed once with cold 1N hydrochloric acid, once with brine, six times with hexane, and again with brine. The solution was dried over sodium sulfate, filtered, and evaporated to dryness to yield 139 mg. of yellow froth. The nmr spectrum of the froth showed the presence of some tri-n-butyltin hydride. The froth was dissolved in acetonitrile and rewashed ten times with hexane, dried and evaporated to yield 14 mg. of the title compound.

EXAMPLE 2

7β-(2-Thienylacetylamino)-3-[1-(4-morpholinyl)-butylideneamino]-3-cephem-4-carboxylic acid To a solution of 1.8 g. of allyl 7β-(2-thienylacetylamino)-3-azido-3-cephem-4-carboxylate in about 100 ml. of 1,2-dichloroethane was added 0.628 g. (1 equiv.) of the enamine formed with n-butyraldehyde and morpholine and the mixture was stirred at room temperature for 1.5 hours. The reaction mixture was evaporated to dryness at 40° C. and the residue chromatographed on silica gel using 10% ethyl acetate in toluene vs. ethyl acetate. Multiple fractions were collected and the fractions containing the product (via tlc) were pooled and evaporated to yield 1.479 g (72.5% yield) of allyl 7β-(2-thienylacetylamino)-3-[1-(4-morpholinyl)butylideneamino]-3-cephem-4-carboxylate.

NMR (T-60 CDCl$_3$): δ 0.9 (m, 3H, CH$_3$), 1.1–1.6 (m, 2H, CH$_2$—CH$_3$), 2.3 (m, 2H, CH$_2$CH$_2$CH$_3$), 2.83, 3.23 (AB J=14 Hz, 2H, C$_2$H), 3.4–3.8 (m, 8H, morpholino H), 3.87 (s, 2H, —CH$_2$-thienyl), 4.57 (m, 2H, —O—CH$_2$—CH═CH$_2$), 5.0–6.0 (m, 5H, C$_5$H, C$_6$H, and allyl vinyl H).

The allyl ester was deesterified to provide the free acid as follows. To a solution of 0.012 g. of palladium diacetate in about 1 ml. of acetone was added 0.033 g of triphenylphosphine and the solution was stirred for about 5 minutes to allow formation of Pd(Pφ$_3$)$_4$. A solution of 0.519 g of the allyl ester in 5 ml. of acetone was added to the solution and the suspension was stirred at ice bath temperature for 10 minutes. Next, 0.349 g of tri-n-butyltin hydride was added and the reaction mixture was stirred without cooling for 22 hours. The reaction mixture was evaporated to dryness and the residue dissolved in cold acetonitrile. The solution was washed once with cold 1N hydrochloric acid, three times with hexane, and once with brine and dried over sodium sulfate. The washed and dried solution was evaporated to dryness to yield 0.229 g. (48%) of the title acid.

EXAMPLE 3 p-Nitrobenzyl 7β-(2-thienylacetylamino)-3-[(dihydro-2(3H)-furanylidene)amino]-3-cephem-4-carboxylate A mixture of 852 mg. of p-nitrobenzyl 7β-(2-thienylacetylamino)-3-azido-3-cephem-4-carboxylate and 20 ml. of 2,3-dihydrofuran was heated at the reflux temperature (54°–55° C.) for 15 minutes. The mixture was evaporated to dryness and the residue chromatographed over 8 g. of silica gel (toluene) using 400 ml. of 5% ethyl acetate in toluene vs. 400 ml. of ethyl acetate. Multiple fractions were collected and fractions containing the product were pooled and evaporated to dryness to give 559 mg. of the title compound.

MS (field desorption) 542

IR (chloroform) 1765 cm$^{-1}$, β-lactam carbonyl

NMR (DMSOd$_6$, 270 MHz): δ 2.00 (m, 2H, HA), 2.50 (m, 2H, Hb), 3.46 (s, 2H, C$_2$H), 4.23 (m, 2H, Hc), 5.16 (d J=4 Hz, C$_6$H), 5.32 (AB, 2H, pNB methylene), 5.54 (d, d J=4.8 Hz, 1H, C$_6$H), 9.12 (d, J=8 Hz, 1H, NH).

UV (C$_2$H$_5$OH) λ$_{max}$ 237 nm (ε=9,600); λ$_{max}$ 270 nm (ε=9,800).

The p-nitrobenzyl ester group of the product ester was removed by incubation with chicken liver esterase and the free acid evaluated for antibacterial activity in the Disc-Plate test. The free acid exhibited zones of inhibition against *Micrococcus luteus* and *Escherichia coli* at concentrations of 10 mg./ml. and 1 mg./ml.

EXAMPLE 4 p-Nitrobenzyl 7β-(2-thienylacetylamino)-3-[(tetrahydro-2-hydroxy-2-furanyl)amino]-3-cephem-4-carboxylate The tetrahydrofuranylidineamino compound obtained as described by Example 3 (0.410 g) was dissolved in 40 ml. of methyl alcohol and the solution heated at the reflux temperature for 2 hours. The solution was evaporated to dryness and the reaction product mixture chromatographed on 8 g. of silica gel set in toluene using 400 ml. of 10% ethyl acetate in toluene vs. 400 ml. of ethyl acetate. Multiple fractions were collected and all fractions containing the same product (tlc) were combined and evaporated to dryness. There were obtained 0.129 g (36%) of the 3-amino ester, p-nitrobenzyl 7β-(2-thienylacetylamino)-3-amino-3-cephem-4-carboxylate and 0.119 g. (28%) of the title compound.

MS (field desorption) 560, 543 (M-18)

IR (chloroform) 1780 cm$^{-1}$ (β-lactam carbonyl)

UV (C$_2$H$_5$OH) λ$_{max}$ 236 nm ε=8,400; λ$_{max}$ 275 nm ε=8,300.

NMR (CDCl$_3$, 60 MHz) δ 2.0 (m, 2H, HA), 2.4–4.3 (m, 2H, HB), 3.7 (AB, 2H, C$_2$H$_2$), 3.90 (s, 2H, thienylacetyl methylene), 4.42 (m, 2H, Hc), 5.05 (d, J=4 Hz, 1H, C$_6$H), 5.37 (m, 2H, pNB methylene), 5.63 (dd, J=4, 8H)

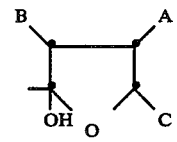

EXAMPLE 5 p-Nitrobenzyl 7β-(2-thienylacetylamino)-3-[(tetrahydro-2H-pyran-2-ylidene)amino]-3-cephem-4-carboxylate p-Nitrobenzyl 7β-(2-thienylacetylamino)-3-azido-3-cephem-4-carboxylate, 500 mg., and 25 ml. of 2,3-dihydropyran were mixed and heated at the reflux temperature for 15 minutes. The reaction mixture was evaporated to dryness and the reaction product mixture chromatographed over 8 g. of silica gel (toluene) using 500 ml. of 5% ethyl acetate in toluene vs. 500 ml. of ethyl acetate. Multiple fractions were collected and all fractions containing the same product (tlc) were combined and evaporated to dryness.

There were obtained 0.137 g (24.6% yield) of the title (product 1) compound and 0.261 g (45.4% yield) of the corresponding hydroxylated compound, p-nitrobenzyl 7β-(2-thienylacetylamino)-3-[(tetrahydro-2-hydroxy-2H-pyran-2-yl)amino]-3-cephem-4-carboxylated (product 2).

Product 1

MS (field desorption) 556, 474 (M-82).

IR (chloroform) 1765 cm$^{-1}$ (β-lactam carbonyl).

UV (C$_2$H$_5$OH) λ$_{max}$ 236 nm (ε=16,000); λ$_{max}$ 276 nm (ε=14,800).

Product 2

MS (field desorption) 574, 474

IR (chloroform) 1775 cm$^{-1}$ (β-lactam carbonyl)

UV (C$_2$H$_5$OH) λ$_{max}$ 236 nm (ε=10,800); λ$_{max}$ 270 nm (ε=9.800).

EXAMPLE 6 p-Nitrobenzyl 7β-(2-thienylacetylamino)-3-[1-(4-morpholinyl)-7-azabicyclo[4.1.0]hept-7-yl]-3-cephem-4-carboxylate To a solution of 0.5 g. of p-nitrobenzyl 7β-(2-thienylacetylamino)-3-azido-3-cephem-4-caraboxylate in 35 ml. of methylene chloride was added 0.167 g. (1 equivalent) of the morpholine enamine of cyclohexanone. The reaction mixture was stirred at room temperature for 18 hours and was evaporated to dryness. The reaction product mixture was chromatographed over silica gel packed in the column with toluene and using 400 ml. of 10% ethyl acetate in toluene vs. 400 ml. of ethyl acetate. The fractions containing the product (tlc) were combined and evaporated to dryness to give the title compound in 28.6% yield.

MS (fast atom bombardment) 640
MS (field desorption) 639
IR )chloroform) 1773 cm$^{-1}$ (β-lactam carbonyl)
UV (C$_2$H$_5$OH) λ$_{max}$ 266 nm ε=11,000

I claim:

1. A compound of the formula

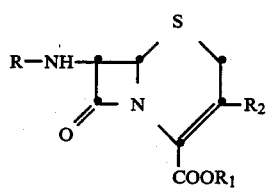

wherein R is hydrogen or an acyl group of the formula

wherein R$^1$ is C$_1$-C$_4$ alkyl, C$_1$-C$_4$ alkyl substituted by halogen or cyano;

or R is an aroyl or aralkanoyl group of the formula

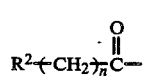

wherein R$^2$ is phenyl or a mono-substituted phenyl group of the formula

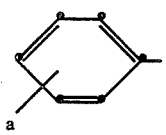

wherein a is halogen, amino, hydroxy, C$_1$-C$_4$ alkyl, C$_1$-C$_4$ alkoxy, cyano, hydroxymethyl, aminomethyl, carboxamido, carboxymethyl, or C$_1$-C$_4$ alkoxycarbonylmethyl;

or R$^2$ is a di- or tri-substituted phenyl group of the formula

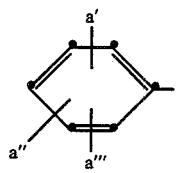

wherein a', a'', and a''' are independently hydrogen, halogen, hydroxy, C$_1$-C$_4$ alkyl, or C$_1$-C$_4$ alkoxy; and n is 0 or 1;

or R is a heteroarylalkanoyl group of the formula

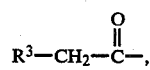

wherein R$^3$ is

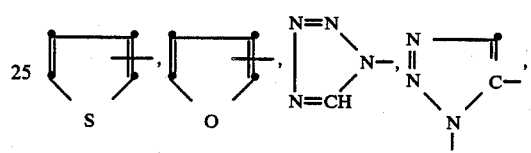

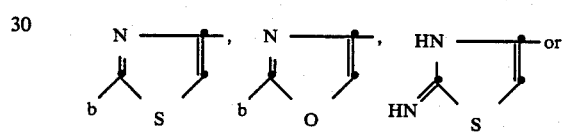

wherein each b is amino, protected amino, C$_1$-C$_3$ alkyl or phenyl;

or R is an aryloxyacetyl or arylthioacetyl group of the formula

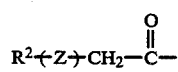

wherein R$^2$ has the same meanings as defined above and Z is O or S;

or R is an α-substituted aralkanoyl or heteroarylalkanoyl substituted group of the formula

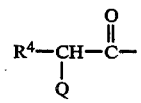

wherein R$^4$ is R$^2$, as defined above, and in addition is thienyl, furyl, or 1,4-cyclohexadienyl; Q is hydroxy, formyloxy, carboxy, the sulfo group —SO$_3$H, or amino;

or R is an oximino-substituted aralkanoyl or heteroarylalkanoyl group of the formula

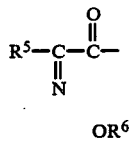

wherein $R^5$ is $R^2$ and $R^3$ as each is defined above, and $R^6$ is hydrogen or $C_1$–$C_3$ alkyl;
$R_1$ is hydrogen or a carboxy protecting group; $R_2$ is a group of the formula

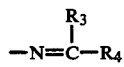

wherein $R_3$ when taken separately is $C_1$–$C_4$ alkyl or $C_1$–$C_4$ alkyl substituted by phenyl or phenyl substituted by one or two $C_1$–$C_4$ alkyl, hydroxy, $C_1$–$C_4$ alkoxy, carboxy, carboxamido, or cyano groups;

$R_4$ when taken separately is $C_1$–$C_4$ alkoxy, $C_1$–$C_4$ alkylthio, phenoxy, phenoxy substituted by one or two $C_1$–$C_4$ alkyl, hydroxy, $C_1$–$C_4$ alkoxy, carboxy, carboxamido, or cyano groups, phenylthio and phenylthio substituted by one or two $C_1$–$C_4$ alkyl, hydroxy, $C_1$–$C_4$ alkoxy, carboxy, carboxamido, or cyano groups; or $R_4$ is an amino group of the formula

wherein $R_4'$ and $R_4''$ are independently $C_1$–$C_4$ alkyl, phenyl or phenyl substituted by one or two $C_1$–$C_4$ alkyl, hydroxy, $C_1$–$C_4$ alkoxy, carboxy, carboxamido, or cyano groups, and $R_4'$ and $R_4''$ when taken together with the nitrogen atom to which they are attached form a 5–6 membered heterocyclic ring of the formula

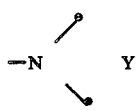

wherein Y is $(-CH_2-)_n$ or $-CH_2-Y'-CH_2-$, wherein n is 2 or 3 and Y' is O, S, or

wherein Y'' is hydrogen, $C_1$–$C_4$ alkyl, or benzyl;
$R_3$ and $R_4$ when taken together with the carbon atom to which they are attached form a 5–7 membered ring of formula

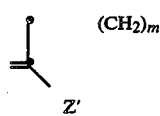

wherein Z' is O or S and m is 2 to 4; or $R_2$ is a group of the formula

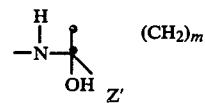

wherein m and Z' have the same meanings as defined above; or $R_2$ is a bicyclic aziridine group of the formula

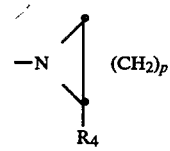

wherein p is 3 to 5, and $R_4$ has the same meanings as defined above;
and when $R_1$ is hydrogen, the pharmaceutically acceptable non-toxic salts thereof.

2. The compound of claim 1 wherein $R_2$ is a group of the formula

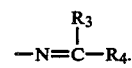

3. The compound of claim 2 wherein $R_3$ is $C_1$–$C_4$ alkyl and $R_4$ is $C_1$–$C_4$ alkoxy.

4. The compound of claim 3, which is 7β-(2-thienylacetylamino)-3-[1-(ethoxyethylidene)amino]-3-cephem-4-carboxylic acid, and the pharmaceutically acceptable non-toxic salts thereof.

5. The compound of claim 2 wherein $R_3$ is $C_1$–$C_4$ alkyl and $R_4$ is a heterocyclic ring.

6. The compound of claim 5 7β-(2-thienylacetylamino)-3-[1-(4-morpholinyl)-butylideneamino]-3-cephem-4-carboxylic acid and the pharmaceutically acceptable non-toxic salts thereof.

7. The compound of claim 2 wherein $R_3$ and $R_4$ are taken together to form a 5–7 membered ring of the formula

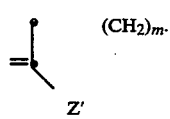

8. The compound of claim 7, 7β-(2-thienylacetylamino)-3-[(tetrahydro-2H-pyran-2-ylidene)amino]-3-cehem-4-carboxylic acid, and the pharmaceutically acceptable non-toxic salts thereof.

9. The compound of claim 7, 7β-(2-thienylacetylamino)-3-[(dihydro-2(3H)-furanylidene)amino]-3-cephem-4-carboxylic acid, and the pharmaceutically acceptable non-toxic salts thereof.

10. The compound of claim 1 wherein $R_2$ is a group of the formula

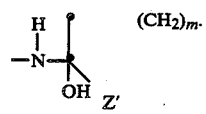

11. The compound of claim 1 wherein $R_2$ is a bicyclic aziridine group of the formula

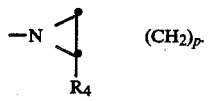

12. The compound of claim 1 wherein $R_1$ is a carboxy-protecting group.

13. The compound of claim 12 wherein $R_1$ is allyl, p-nitrobenzyl, p-methoxybenzyl or diphenylmethyl.

14. The compound of claim 13 wherein $R_1$ is allyl.

15. The compound of claim 1 wherein R is an aralkanoyl group of the formula

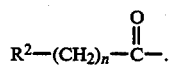

16. The compound of claim 1 wherein R is an acyl group of the formula

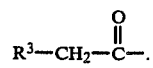

17. The compound of claim 1 wherein R is an acyl group of the formula

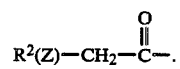

18. The compound of claim 1 wherein R is an acyl group of the formula

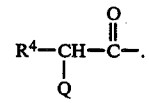

19. The compound of claim 1 wherein R is an acyl group of the formula

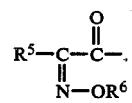

20. The compound of claim 1 wherein R is hydrogen.

* * * * *

UNITED STATES PATENT AND TRADEMARK OFFICE
CERTIFICATE OF CORRECTION

PATENT NO. : 4,560,749
DATED : December 24, 1985
INVENTOR(S) : Douglas O. Spry

It is certified that error appears in the above—identified patent and that said Letters Patent is hereby corrected as shown below:

Column 4, lines 1-7,

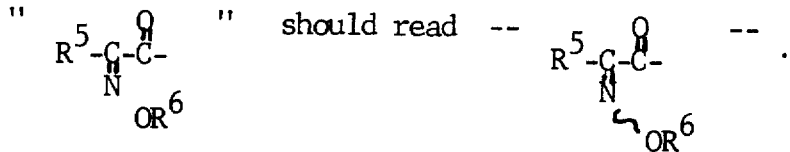

Column 4, lines 35-40,

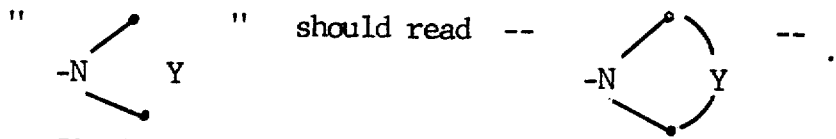

Column 4, lines 53-57,

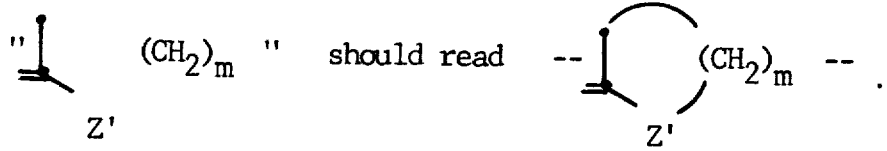

UNITED STATES PATENT AND TRADEMARK OFFICE
CERTIFICATE OF CORRECTION

PATENT NO. : 4,560,749
DATED : December 24, 1985
INVENTOR(S) : Douglas O. Spry

It is certified that error appears in the above—identified patent and that said Letters Patent is hereby corrected as shown below:

Column 4, lines 63-68,

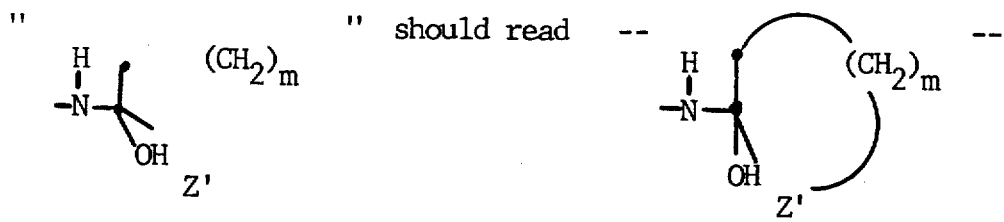

Column 5, lines 6-10,

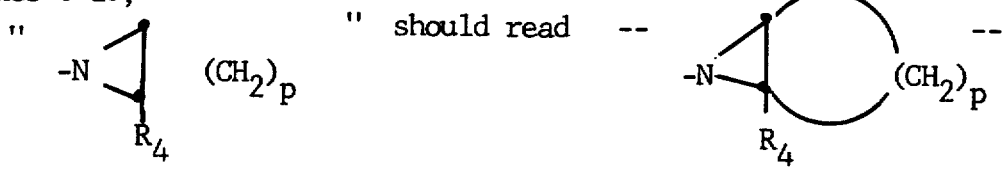

Column 7, lines 56-59,

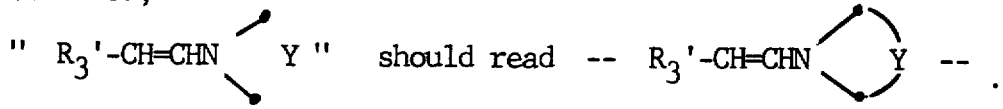

Column 8, lines 32-34,

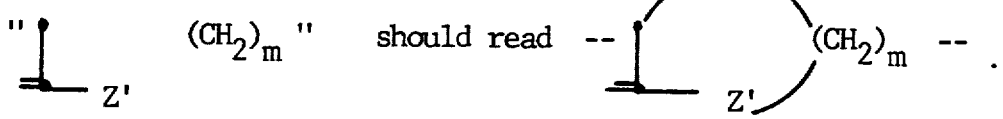

UNITED STATES PATENT AND TRADEMARK OFFICE
CERTIFICATE OF CORRECTION

PATENT NO. : 4,560,749

DATED : December 24, 1985

INVENTOR(S) : Douglas O. Spry

It is certified that error appears in the above—identified patent and that said Letters Patent is hereby corrected as shown below:

Column 8, lines 44-49,

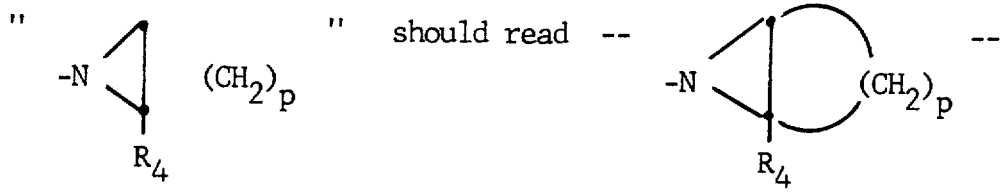

Column 8, lines 57-60,

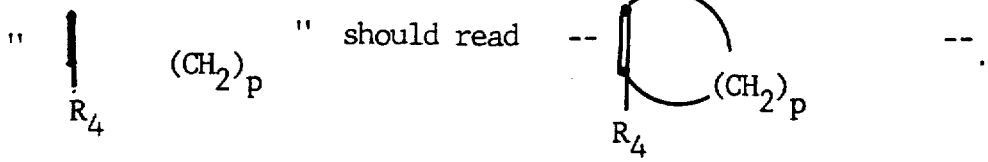

Column 9, lines 4-7,

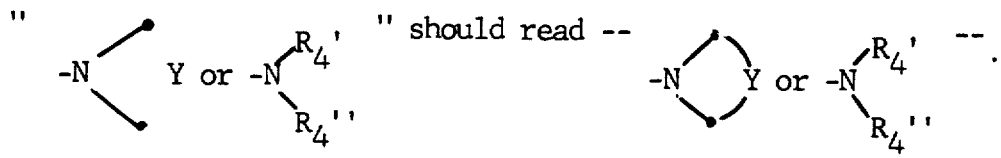

UNITED STATES PATENT AND TRADEMARK OFFICE
CERTIFICATE OF CORRECTION

PATENT NO. : 4,560,749

DATED : December 24, 1985

INVENTOR(S) : Douglas O. Spry

It is certified that error appears in the above—identified patent and that said Letters Patent is hereby corrected as shown below:

Column 9, lines 35-39,

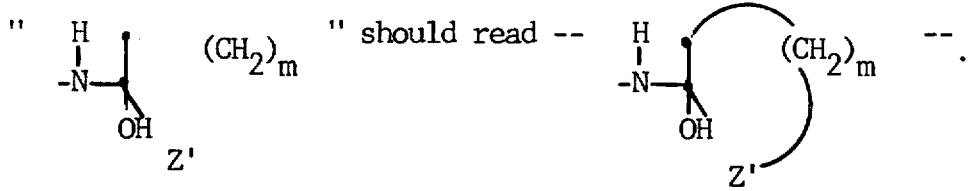

Column 9, lines 45-49,

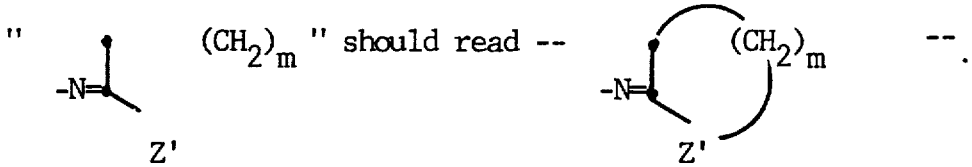

Column 9, lines 56-62, that portion of the structural formula reading

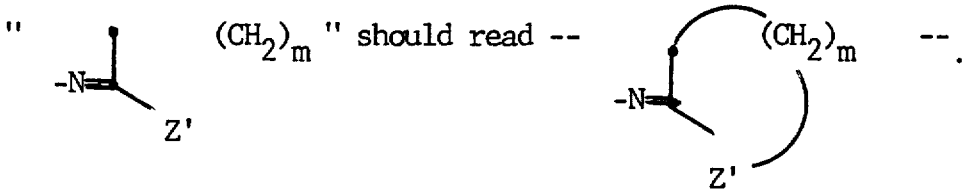

UNITED STATES PATENT AND TRADEMARK OFFICE
CERTIFICATE OF CORRECTION

PATENT NO. : 4,560,749
DATED : December 24, 1985
INVENTOR(S) : Douglas O. Spry

It is certified that error appears in the above—identified patent and that said Letters Patent is hereby corrected as shown below:

Column 12, lines 22-26,

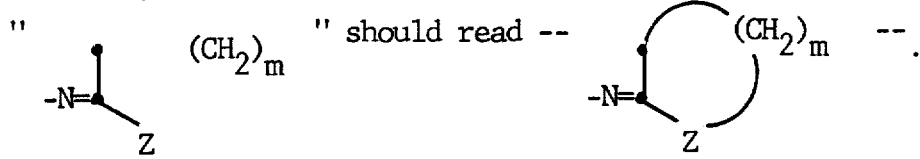

Column 17, line 23, "IR )chloroform)" should read -- IR (chloroform) --.

Column 19, lines 1-7,

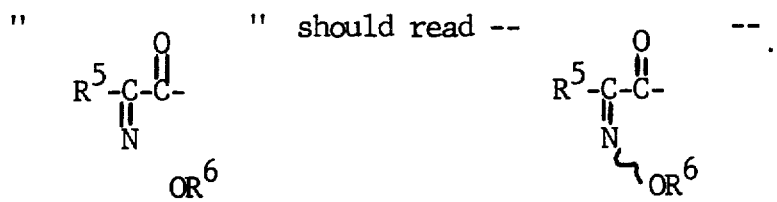

Column 19, lines 44-48,

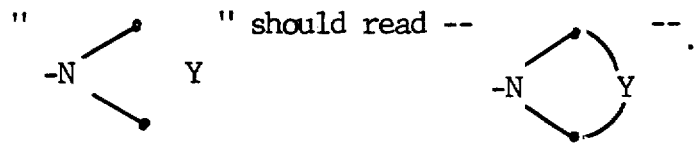

UNITED STATES PATENT AND TRADEMARK OFFICE
CERTIFICATE OF CORRECTION

PATENT NO. : 4,560,749

DATED : December 24, 1985

INVENTOR(S) : Douglas O. Spry

It is certified that error appears in the above—identified patent and that said Letters Patent is hereby corrected as shown below:

Column 19, lines 61-65,

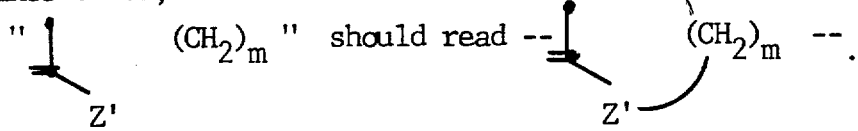

Column 20, lines 1-6,

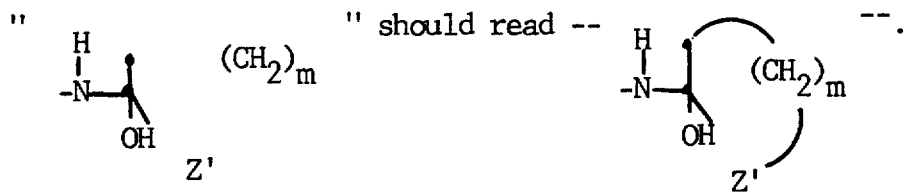

Column 20, lines 12-18,

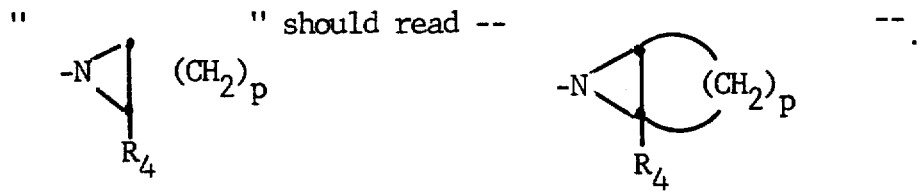

UNITED STATES PATENT AND TRADEMARK OFFICE
CERTIFICATE OF CORRECTION

PATENT NO. : 4,560,749

DATED : December 24, 1985

INVENTOR(S) : Douglas O. Spry

It is certified that error appears in the above—identified patent and that said Letters Patent is hereby corrected as shown below:

Column 20, lines 51-56,

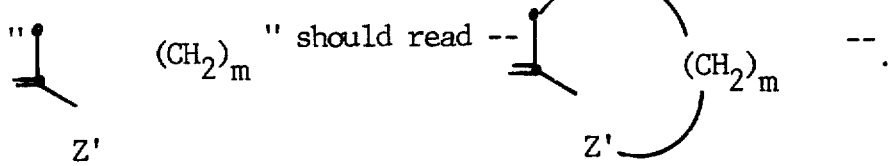

Column 20, line 60, "ylidene)amino̲/-3-cehem-4-carboxylic" should read -- ylidene)amino̲/-3-cephem-4-carb̄oxylic --.

Column 21, lines 1-8,

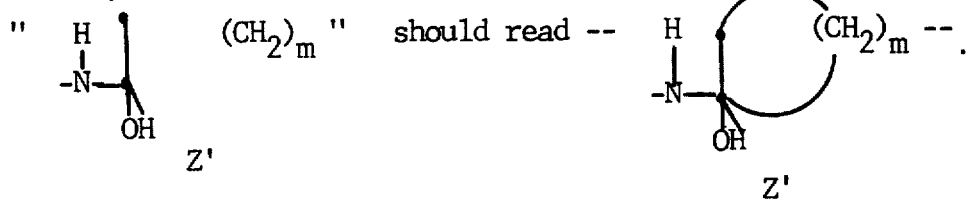

UNITED STATES PATENT AND TRADEMARK OFFICE
CERTIFICATE OF CORRECTION

PATENT NO. : 4,560,749

DATED : December 24, 1985

INVENTOR(S) : Douglas O. Spry

It is certified that error appears in the above-identified patent and that said Letters Patent is hereby corrected as shown below:

Column 21, lines 14-18,

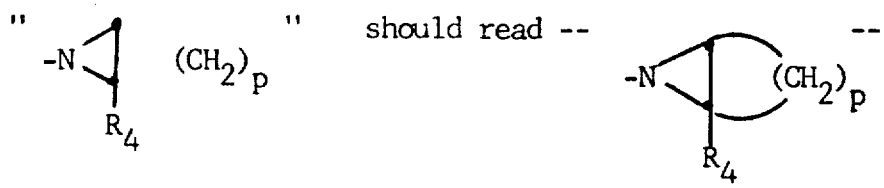

Signed and Sealed this

Twenty-sixth Day of August 1986

[SEAL]

Attest:

DONALD J. QUIGG

Attesting Officer

Commissioner of Patents and Trademarks